(12) United States Patent
Tracey et al.

(10) Patent No.: US 8,391,970 B2
(45) Date of Patent: Mar. 5, 2013

(54) DEVICES AND METHODS FOR INHIBITING GRANULOCYTE ACTIVATION BY NEURAL STIMULATION

(75) Inventors: Kevin J. Tracey, Old Greenwich, CT (US); Howland Shaw Warren, Cambridge, MA (US); Christine N. Metz, Great Neck, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 789 days.

(21) Appl. No.: 12/198,808

(22) Filed: Aug. 26, 2008

(65) Prior Publication Data

US 2009/0062874 A1   Mar. 5, 2009

Related U.S. Application Data

(60) Provisional application No. 60/968,292, filed on Aug. 27, 2007.

(51) Int. Cl.
*A61N 1/00* (2006.01)

(52) U.S. Cl. ............................................. 607/2; 607/62

(58) Field of Classification Search .................. 607/1, 2, 607/62
See application file for complete search history.

(56) References Cited

U.S. PATENT DOCUMENTS

| | | | |
|---|---|---|---|
| 2,164,121 A | 6/1939 | Pescador | |
| 3,363,623 A | 1/1968 | Atwell | |
| 4,073,296 A | 2/1978 | McCall | |
| 4,098,277 A | 7/1978 | Mendell | |
| 4,305,402 A | 12/1981 | Katims | |
| 4,503,863 A | 3/1985 | Katims | |
| 4,573,481 A | 3/1986 | Bullara | |
| 4,590,946 A | 5/1986 | Loeb | |
| 4,632,095 A | 12/1986 | Libin | |
| 4,649,936 A | 3/1987 | Ungar et al. | |
| 4,702,254 A | 10/1987 | Zabara | |
| 4,840,793 A | 6/1989 | Todd, III et al. | |
| 4,867,164 A | 9/1989 | Zabara | |
| 4,929,734 A | 5/1990 | Coughenour et al. | |
| 4,935,234 A | 6/1990 | Todd, III et al. | |
| 4,979,511 A | 12/1990 | Terry, Jr. | |
| 4,991,578 A | 2/1991 | Cohen | |
| 5,019,648 A | 5/1991 | Schlossman et al. | |
| 5,025,807 A | 6/1991 | Zabara | |
| 5,049,659 A | 9/1991 | Cantor et al. | |

(Continued)

FOREIGN PATENT DOCUMENTS

| | | |
|---|---|---|
| DE | 2628045 A1 | 1/1977 |
| DE | 3736664 A1 | 5/1989 |

(Continued)

OTHER PUBLICATIONS

Abraham, Coagulation abnormalities in acute lung injury and sepsis, Am. J. Respir. Cell Mol. Biol., vol. 22, pp. 401-404, 2000.

(Continued)

*Primary Examiner* — Scott Getzow
(74) *Attorney, Agent, or Firm* — Shay Glenn LLP

(57) ABSTRACT

Described herein are methods, devices and systems for inhibition of granulocyte activation by appropriate stimulation of the vagus nerve. Methods of treating granulocyte-mediated disorders (including inflammatory disorders) by stimulating the vagus nerve to inhibit granulocyte activation (particularly neutrophil activation) are also described. Appropriate stimulation may be very low levels of stimulation, including stimulation that does not result in desensitization. The level of granulocyte activation may be detected and used to at least partially control stimulation.

27 Claims, 7 Drawing Sheets

U.S. PATENT DOCUMENTS

| | | |
|---|---|---|
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thomspon et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 * | 9/2003 | Boveja ............................ 607/45 |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |

| | | |
|---|---|---|
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,195,287 B2 | 6/2012 | Dacey, Jr. et al. |
| 8,214,056 B2 | 7/2012 | Hoffer et al. |
| 2001/0002441 A1 | 5/2001 | Boveja |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1* | 7/2004 | Tan et al. ................. 435/7.2 |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0236381 A1 | 11/2004 | Dinsmoor et al. |
| 2004/0236382 A1 | 11/2004 | Dinsmoor et al. |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0125044 A1 | 6/2005 | Tracey et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0251220 A1 | 11/2005 | Barrett et al. |
| 2005/0251222 A1 | 11/2005 | Barrett et al. |

| | | | | | | |
|---|---|---|---|---|---|---|
| 2005/0267542 A1 | 12/2005 | David et al. | | 2007/0027498 A1 | 2/2007 | Maschino et al. |
| 2005/0267547 A1 | 12/2005 | Knudson et al. | | 2007/0027499 A1 | 2/2007 | Maschino et al. |
| 2005/0282906 A1 | 12/2005 | Tracey et al. | | 2007/0027500 A1 | 2/2007 | Maschino et al. |
| 2005/0283198 A1 | 12/2005 | Haubrich et al. | | 2007/0027504 A1 | 2/2007 | Barrett et al. |
| 2006/0009815 A1 | 1/2006 | Boveja et al. | | 2007/0055324 A1 | 3/2007 | Thompson et al. |
| 2006/0015151 A1 | 1/2006 | Aldrich | | 2007/0067004 A1 | 3/2007 | Boveja et al. |
| 2006/0025828 A1 | 2/2006 | Armstrong et al. | | 2007/0083242 A1 | 4/2007 | Mazgalev et al. |
| 2006/0036293 A1 | 2/2006 | Whitehurst et al. | | 2007/0093434 A1 | 4/2007 | Rossetti et al. |
| 2006/0052657 A9 | 3/2006 | Zabara | | 2007/0093870 A1 | 4/2007 | Maschino |
| 2006/0052831 A1 | 3/2006 | Fukui | | 2007/0093875 A1 | 4/2007 | Chavan et al. |
| 2006/0052836 A1 | 3/2006 | Kim et al. | | 2007/0100263 A1 | 5/2007 | Merfeld |
| 2006/0058851 A1 | 3/2006 | Cigaina | | 2007/0100377 A1 | 5/2007 | Armstrong et al. |
| 2006/0064137 A1 | 3/2006 | Stone | | 2007/0100378 A1 | 5/2007 | Maschino |
| 2006/0064139 A1 | 3/2006 | Chung et al. | | 2007/0100380 A1 | 5/2007 | Fukui |
| 2006/0074450 A1 | 4/2006 | Boveja et al. | | 2007/0100392 A1 | 5/2007 | Maschino et al. |
| 2006/0074473 A1 | 4/2006 | Gertner | | 2007/0106339 A1 | 5/2007 | Errico et al. |
| 2006/0079936 A1 | 4/2006 | Boveja et al. | | 2007/0118177 A1 | 5/2007 | Libbus et al. |
| 2006/0085046 A1 | 4/2006 | Rezai et al. | | 2007/0118178 A1 | 5/2007 | Fukui |
| 2006/0095081 A1 | 5/2006 | Zhou et al. | | 2007/0129780 A1 | 6/2007 | Whitehurst et al. |
| 2006/0095090 A1 | 5/2006 | De Ridder | | 2007/0135846 A1 | 6/2007 | Knudson et al. |
| 2006/0100668 A1 | 5/2006 | Ben-David et al. | | 2007/0135856 A1 | 6/2007 | Knudson et al. |
| 2006/0111644 A1 | 5/2006 | Guttag et al. | | 2007/0135857 A1 | 6/2007 | Knudson et al. |
| 2006/0111754 A1 | 5/2006 | Rezai et al. | | 2007/0135858 A1 | 6/2007 | Knudson et al. |
| 2006/0111755 A1 | 5/2006 | Stone et al. | | 2007/0142870 A1 | 6/2007 | Knudson et al. |
| 2006/0116739 A1 | 6/2006 | Betser et al. | | 2007/0142871 A1 | 6/2007 | Libbus et al. |
| 2006/0122675 A1 | 6/2006 | Libbus et al. | | 2007/0142874 A1 | 6/2007 | John |
| 2006/0129200 A1 | 6/2006 | Kurokawa | | 2007/0150006 A1 | 6/2007 | Libbus et al. |
| 2006/0129202 A1 | 6/2006 | Armstrong | | 2007/0150011 A1 | 6/2007 | Meyer et al. |
| 2006/0135998 A1 | 6/2006 | Libbus et al. | | 2007/0150021 A1 | 6/2007 | Chen et al. |
| 2006/0142802 A1 | 6/2006 | Armstrong | | 2007/0150027 A1 | 6/2007 | Rogers |
| 2006/0142822 A1 | 6/2006 | Tulgar | | 2007/0156180 A1 | 7/2007 | Jaax et al. |
| 2006/0149337 A1 | 7/2006 | John | | 2007/0239243 A1 | 10/2007 | Moffitt et al. |
| 2006/0161216 A1 | 7/2006 | John et al. | | 2007/0250145 A1 | 10/2007 | Kraus et al. |
| 2006/0161217 A1 | 7/2006 | Jaax et al. | | 2007/0255320 A1 | 11/2007 | Inman et al. |
| 2006/0167497 A1 | 7/2006 | Armstrong et al. | | 2007/0255333 A1 | 11/2007 | Giftakis |
| 2006/0167498 A1 | 7/2006 | DiLorenzo | | 2008/0021517 A1 | 1/2008 | Dietrich |
| 2006/0167501 A1 | 7/2006 | Ben-David et al. | | 2008/0021520 A1 | 1/2008 | Dietrich |
| 2006/0173493 A1 | 8/2006 | Armstrong et al. | | 2008/0046055 A1 | 2/2008 | Durand et al. |
| 2006/0173508 A1 | 8/2006 | Stone et al. | | 2008/0058871 A1 | 3/2008 | Libbus et al. |
| 2006/0178691 A1 | 8/2006 | Binmoeller | | 2008/0103407 A1 | 5/2008 | Bolea et al. |
| 2006/0178703 A1* | 8/2006 | Huston et al. ............... 607/2 | | 2008/0140138 A1 | 6/2008 | Ivanova et al. |
| 2006/0178706 A1 | 8/2006 | Lisogurski et al. | | 2008/0183246 A1 | 7/2008 | Patel et al. |
| 2006/0190044 A1 | 8/2006 | Libbus et al. | | 2008/0234790 A1 | 9/2008 | Bayer et al. |
| 2006/0200208 A1 | 9/2006 | Terry, Jr. et al. | | 2008/0249439 A1 | 10/2008 | Tracey et al. |
| 2006/0200219 A1 | 9/2006 | Thrope et al. | | 2008/0281365 A1 | 11/2008 | Tweden et al. |
| 2006/0206155 A1 | 9/2006 | Ben-David et al. | | 2009/0012590 A1 | 1/2009 | Inman et al. |
| 2006/0206158 A1 | 9/2006 | Wu et al. | | 2009/0048194 A1 | 2/2009 | Aerssens et al. |
| 2006/0229677 A1 | 10/2006 | Moffitt et al. | | 2009/0105782 A1 | 4/2009 | Mickle et al. |
| 2006/0229681 A1 | 10/2006 | Fischell | | 2009/0123521 A1 | 5/2009 | Weber et al. |
| 2006/0241699 A1 | 10/2006 | Libbus et al. | | 2009/0125079 A1 | 5/2009 | Armstrong et al. |
| 2006/0247719 A1 | 11/2006 | Maschino et al. | | 2009/0177112 A1 | 7/2009 | Gharib et al. |
| 2006/0247721 A1 | 11/2006 | Maschino et al. | | 2009/0187231 A1 | 7/2009 | Errico et al. |
| 2006/0247722 A1 | 11/2006 | Maschino et al. | | 2009/0254143 A1 | 10/2009 | Tweden et al. |
| 2006/0259077 A1 | 11/2006 | Pardo et al. | | 2009/0276019 A1 | 11/2009 | Perez et al. |
| 2006/0259084 A1 | 11/2006 | Zhang et al. | | 2009/0281593 A9 | 11/2009 | Errico et al. |
| 2006/0259085 A1 | 11/2006 | Zhang et al. | | 2010/0003656 A1 | 1/2010 | Kilgard et al. |
| 2006/0259107 A1 | 11/2006 | Caparso et al. | | 2010/0010603 A1 | 1/2010 | Ben-David et al. |
| 2006/0271115 A1 | 11/2006 | Ben-Ezra et al. | | 2010/0042186 A1 | 2/2010 | Ben-David et al. |
| 2006/0282121 A1 | 12/2006 | Payne et al. | | 2010/0063563 A1 | 3/2010 | Craig |
| 2006/0282131 A1 | 12/2006 | Caparso et al. | | 2010/0125304 A1 | 5/2010 | Faltys |
| 2006/0282145 A1 | 12/2006 | Caparso et al. | | 2010/0215632 A1 | 8/2010 | Boss et al. |
| 2006/0287678 A1 | 12/2006 | Shafer | | 2010/0241183 A1 | 9/2010 | DiLorenzo |
| 2006/0287679 A1 | 12/2006 | Stone | | 2010/0249859 A1 | 9/2010 | DiLorenzo |
| 2006/0293720 A1 | 12/2006 | DiLorenzo | | 2010/0280569 A1 | 11/2010 | Bobillier et al. |
| 2006/0293721 A1 | 12/2006 | Tarver et al. | | 2011/0004266 A1 | 1/2011 | Sharma |
| 2006/0293723 A1 | 12/2006 | Whitehurst et al. | | 2011/0066208 A1 | 3/2011 | Pasricha et al. |
| 2007/0016262 A1 | 1/2007 | Gross et al. | | 2011/0106208 A1 | 5/2011 | Faltys et al. |
| 2007/0016263 A1 | 1/2007 | Armstrong et al. | | 2012/0065706 A1 | 3/2012 | Vallapureddy et al. |
| 2007/0021785 A1 | 1/2007 | Inman et al. | | | | |
| 2007/0021786 A1 | 1/2007 | Parnis et al. | | FOREIGN PATENT DOCUMENTS | | |
| 2007/0021814 A1 | 1/2007 | Inman et al. | | DE | 20316509 U1 | 4/2004 |
| 2007/0025608 A1 | 2/2007 | Armstrong | | EP | 0 438 510 B1 | 8/1996 |
| 2007/0027482 A1 | 2/2007 | Parnis et al. | | EP | 0 726 791 B1 | 6/2000 |
| 2007/0027483 A1 | 2/2007 | Maschino et al. | | EP | 1 001 827 B1 | 1/2004 |
| 2007/0027484 A1 | 2/2007 | Guzman et al. | | EP | 2 073 896 B1 | 10/2011 |
| 2007/0027486 A1 | 2/2007 | Armstrong | | GB | 04133 | 0/1910 |
| 2007/0027492 A1 | 2/2007 | Maschino et al. | | WO | WO93/01862 A1 | 2/1993 |
| 2007/0027496 A1 | 2/2007 | Parnis et al. | | WO | WO97/30998 A1 | 8/1997 |
| 2007/0027497 A1 | 2/2007 | Parnis | | WO | WO98/20868 A1 | 5/1998 |

| | | | |
|---|---|---|---|
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO04/000413 A2 | 12/2003 |
| WO | WO2004/064918 A1 | 8/2004 |
| WO | WO2006/073484 A1 | 7/2006 |
| WO | WO 2007/133718 A2 | 11/2007 |

OTHER PUBLICATIONS

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Antonica, A., et al., Vagal control of lymphocyte release from rat thymus, J. Auton. Nerv. Syst., vol. 48, pp. 187-197, 1994.

Asakura et al., Non-surgical therapy for ulcerative colitis, Nippon Geka Gakkai Zasshi, vol. 98, No. 4, pp. 431-437, Apr. 1997 (abstract only).

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression IN shock, New York Surgical Society, New York, NY, Apr. 11, 2001.

Bernik, et al., Pharmacological stimulation of the cholinergic anti-inflammatory pathway, The Journal of Experimental Medicine, vol. 195, No. 6, pp. 781-788, Mar. 18, 2002.

Bhattacharya, S.K. et al., Central muscarinic receptor subtypes and carrageenin-induced paw oedema in rats, Res. Esp. Med. vol. 191, pp. 65-76, 1991.

Bianchi et al., Suppression of proinflammatory cytokines in monocytes by a tetravalent guanylhydrazone, Journal of Experimental Medicine, vol. 183, pp. 927-936, Mar. 1996.

Blum, A. et al., Role of cytokines in heart failure, Am. Heart J., vol. 135, pp. 181-186, 1998.

Boldyreff, Gastric and intestinal mucus, its properties and physiological importance, Acta Medica Scandinavica (journal), vol. 89, pp. 1-14, 1936.

Borovikova et al., Efferent vagus nerve activity attenuates cytokine-mediated inflammation, Society for Neuroscience Abstracts, vol. 26, No. 102, 2000 (abstract only).

Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.

Borovikova et al., Role of the efferent vagus nerve signaling in the regulation of the innate immune response to LPS, (supplemental to SHOCK, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.

Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).

Borovikova et al., Vagotomy blocks the protective effects of I.C.V. CNI-1493 against LPS-induced shock, (Supplemental to SHOCK, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.

Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.

Borovikova, L. V., et al., Vagus nerve stimulation attenuates the systemic inflammatory response to endotoxin, Nature, vol. 405, No. 6785: pp. 458-462, May 25, 2000.

Bumgardner, G. L. et al., Transplantation and cytokines, Seminars in Liver Disease, vol. 19, No. 2, pp. 189-204, 1999.

Carteron, N. L., Cytokines in rheumatoid arthritis: trials and tribulations, Mol. Med. Today, vol. 6, pp. 315-323, 2000.

Corcoran, et al., The effects of vagus nerve stimulation on pro- and anti-inflammatory cytokines in humans: a preliminary report, NeuroImmunoModulation, vol. 12, pp. 307-309, 2005.

Dibbs, Z., et al., Cytokines in heart failure: pathogenetic mechanisms and potential treatment, Proc. Assoc. Am. Physicians, vol. 111, No. 5, pp. 423-428, 1999.

Dinarello, C. A., The interleukin-1 family: 10 years of discovery, FASEB J., vol. 8, No. 15, pp. 1314-1325, 1994.

Doshi et al., Evolving role of tissue factor and its pathway inhibitor, Crit. Care Med., vol. 30, suppl. 5, pp. S241-S250, 2002.

Esmon, The protein C pathway, Crit. Care Med., vol. 28, suppl. 9, pp. S44-S48, 2000.

Fleshner, M., et al., Thermogenic and corticosterone responses to intravenous cytokines (IL-1? and TNF-?) are attenuated by subdiaphragmatic vagotomy, J. Neuroimmunol., vol. 86, pp. 134-141, 1998.

Fox, et al., Use of muscarinic agonists in the treatment of Sjorgren' syndrome, Clin. Immunol., vol. 101, No. 3; pp. 249-263, 2001.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, 2000.

Ghia, et al., The vagus nerve: a tonic inhibitory influence associated with inflammatory bowel disease in a murine model, Gastroenterology, vol. 131, pp. 1122-1130, 2006.

Giebelen, et al., Stimulation of ?7 cholinergic receptors inhibits lipopolysaccharide-induced neutrophil recruitment by a tumor necrosis factor ?-independent mechanism, SHOCK, vol. 27, No. 4, pp. 443-447, 2007.

Gracie, J. A., et al., A proinflammatory role for IL-18 in rheumatoid arthritis, J. Clin. Invest., vol. 104, No. 10, pp. 1393-1401, 1999.

Granert et al., Suppression of macrophage activation with CNI-1493 increases survival in infant rats with systemic haemophilus influenzae infection, Infection and Immunity, vol. 68, No. 9, pp. 5329-5334, Sep. 2000.

Hirano, T., Cytokine suppresive agent improves survival rate in rats with acute pancreatitis of closed duodenal loop, J. Surg. Res., vol. 81, No. 2, pp. 224-229, 1999.

Holladay et al., Neuronal nicotinic acetylcholine receptors as targets for drug discovery, Journal of Medicinal Chemistry, 40, pp. 4169-4194, 1997.

Hommes, D. W. et al., Anti- and Pro-inflammatory cytokines in the pathogenesis of tissue damage in Crohn's disease, Current Opinion in Clinical Nutrition and Metabolic Care, vol. 3., pp. 191-195, 2000.

Hsu, H. Y., et al., Cytokine release of peripheral blood monocuclear cells in children with chronic hepatitis B virus infection, J. Pediatr. Gastroenterol., vol. 29, No. 5, pp. 540-545, 1999.

Hu, et al., The effect of norepinephrine on endotoxin-mediated macrophage activation, J. Neuroimmunol., vol. 31, pp. 35-42, 1991.

Jander, S. et al., Interleukin-18 is induced in acute inflammatory demyelinating polymeuropathy, J. Neuroimmunol., vol. 114, pp. 253-258, 2001.

Kanai, T. et al., Interleukin-18 and Crohn's disease, Digestion, vol. 63, suppl. 1, pp. 37-42, 2001.

Katagiri, M., et al., Increased cytokine production by gastric mucosa in patients with *Helicobacter pylori* infection, J. Clin, Gastroenterol., vol. 25, Suppl. 1, pp. S211-S214, 1997.

Kimball, et al., Levamisole causes differential cytokine expression by elicited mouse peritoneal macrophases, Journal of Leukocyte Biology, vo. 52, No. 3, pp. 349-356, 1992 (abstract only).

Kimmings, A. N., et al., Systemic inflammatory response in acute cholangitis and after subsequent treatment, Eur. J. Surg., vol. 166, pp. 700-705, 2000.

Kirchner et al.; Left vagus nerve stimulation suppresses experimentally induced pain; Neurology; vol. 55; pp. 1167-1171; 2000.

Kumins, N. H., et al., Partial hepatectomy reduces the endotoxin-induced peak circulating level of tumor necrosis factor in rats, SHOCK, vol. 5, No. 5, pp. 385-388, 1996.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, 1995.

Lipton, J. M. et al.; Anti-inflammatory actions of the neuroimmunomodulator ?-MSH, Immunol. Today, vol. 18, pp. 140-145, 1997.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

McGuinness, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, 2000.

Minnich et al.; Anti-cytokine and anti-inflammatory therapies for the treatment of severe sepsis: progress and pitfalls; Proceedings of the Nutrition Society; vol. 63; pp. 437-441; 2004.

Molina et al., CNI-1493 attenuates hemodynamic and pro-inflammatory responses to LPS, Shock, vol. 10, No. 5, pp. 329-334, Nov. 1998.

Nathan, C. F., Secretory products of macrophages, J. Clin. Invest., vol. 79, pp. 319-326, 1987.

Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; 2001.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.

Prystowsky, J. B. et al., Interleukin-1 mediates guinea pig gallbladder inflammation in vivo, J. Surg. Res., vol. 71, No. 2, pp. 123-126, 1997.

Pulkki, K. J., Cytokines and cardiomyocyte death, Ann. Med., vol. 29, pp. 339-343, 1997.

Rayner, S. A. et al., Local bioactive tumour necrosis factor (TNF) in corneal allotransplantation, Clin. Exp. Immunol., vol. 122, pp. 109-116, 2000.

Romanovsky, A. A., et al.,The vagus nerve in the thermoregulatory response to systemic inflammation, Am. J. Physiol., vol. 273, No. 1 (part 2), pp. R407-R413, 1997.

Scheinman, R. I., et al., Role of transcriptional activation of I?B? in mediation of immunosuppression by glucocorticoids, Science, vol. 270, pp. 283-286, 1995.

Stalcup et al., Endothelial cell functions in the hemodynamic responses to stress, Annals of the New York Academy of Sciences, vol. 401, pp. 117-131, 1982.

Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.

Tracey et al., Mind over immunity, Faseb Journal, vol. 15, No. 9, pp. 1575-1576, Jul. 2001.

Tracey, K. J. et al., Shock and tissue injury induced by recombinant human cachectin, Science, vol. 234, pp. 470-474, 1986.

Tracey, K.J., The inflammatory reflex, Nature, vol. 420, pp. 853-859, 2002.

Vanhoutte, et al., Muscarinic and beta-adrenergic prejunctional modulation of adrenergic neurotransmission in the blood vessel wall, Gen Pharmac., vol. 14, pp. 35-37, 1983.

vanWesterloo, et al., The cholinergic anti-inflammatory pathway regulates the host response during septic peritonitis, The Journal of Infectious Diseases, vol. 191, pp. 2138-2148, Jun. 15, 2005.

Ventureyra, Transcutaneous vagus nerve stimulation for partial onset seizure therapy, Child's Nery Syst, vol. 16, pp. 101-102, 2000.

Villa et al., Protection against lethal polymicrobial sepsis by CNI-1493, an inhibitor of pro-inflammatory cytokine synthesis, Journal of Endotoxin Research, vol. 4, No. 3, pp. 197-204, 1997.

Von Känal, et al., Effects of non-specific ?-adrenergic stimulation and blockade on blood coagulation in hypertension, J. Appl. Physiol., vol. 94, pp. 1455-1459, 2003.

Waserman, S. et al., TNF-? dysregulation in asthma: relationship to ongoing corticosteroid therapy, Can. Respir. J., vol. 7, No. 3, pp. 229-237, 2000.

Watanabe, H. et al., The significance of tumor necrosis factor (TNF) levels for rejection of joint allograft, J. Reconstr. Microsurg., vol. 13, No. 3, pp. 193-197, 1997.

Watkins, L.R. et al., Implications of immune-to-brain communication for sickness and pain, Proc. Natl. Acad. Sci. U.S.A., vol. 96, pp. 7710-7713, 1999.

Woiciechowsky, C. et al., Sympathetic activation triggers systemic interleukin-10 release in immunodepression induced by brain injury, Nature Med., vol. 4, No. 7, pp. 808-813, 1998.

Yeh, S.S. et al., Geriatric cachexia: the role of cytokines, Am. J. Clin. Nutr., vol. 70, pp. 183-197, 1999.

Zhang et al., Tumor necrosis factor, The Cytokine Handbook, 3rd ed., Ed. Thompson, Academic Press, pp. 517-548, 1998.

Tracey et al.; U.S. Appl. No. 12/109,334 entitled "Inhibition of inflammatory cytokine production by cholinergic agonists and vagus nerve stimulation," filed Apr. 24, 2008.

Ilton et al., "Differential exprossion of neutrophil adhesion molecules during coronary artery surgery with cardiopulmonary bypass" Journal of Thoracic and Cardiovascular Surgery, Mosby-Year Book, inc., St. Louis, Mo, US, pp. 930-937, Nov. 1, 1999.

Shapiro et al.; Prospective, randomised trial of two doses of rFVIIa (NovoSeven) in haemophilia patients with inhibitors undergoing surgery; Thromb Haemost; vol. 80; pp. 773-778; 1998.

Martindale: The extrapharcopoeia; 28th Ed. London; The pharmaceutical press; pp. 446-485; 1982.

Shi et al.; Effects of efferent vagus nerve excitation on inflammatory response in heart tissue in rats with endotoxemia; vol. 15, No. 1; pp. 26-28; 2003 (Eng. Abstract).

Huston et al.; U.S. Appl. No. 12/259,208 entitled "Treating inflammatory disorders by stimulation of the cholinergic anti-inflammatory pathway," filed Oct. 27, 2008.

Huston et al.; Splenectomy inactivates the cholinergic antiinflammatory pathway during lethal endotoxemia and polymicrobial sepsis; J. Exp. Med. 2006; vol. 203; pp. 1623-1628; 2006.

Saghizadeh et al.; The expression of TNF? by human muscle; J. Clin. Invest.; vol. 97; No. 4; pp. 1111-1116; 1996.

Tracey et al.; U.S. Appl. No. 12/415,671 entitled "Methods and systems for reducing inflammation by neuromodulation of T-cell activity," filed Mar. 31, 2009.

Faltys et al.; U.S. Appl. No. 12/434,462 entitled "Vagus nerve stimulation electrodes and methods of use," filed May 1, 2009.

Benthem et al.; Parasympathetic inhibition of sympathetic neural activity to the pancreas; Am.J.Physiol Endocrinol.Metab; 280; pp. E378-E381; 2001.

Bernik et al., Vagus nerve stimulation attenuates cardiac TNF production in endotoxic shock, (supplemental to SHOCK, vol. 15, 2001, Injury, inflammation and sepsis: laboratory and clinical approaches, SHOCK, Abstracts, 24th Annual Conference on Shock, Marco Island, FL, Jun. 9-12, 2001), Abstract No. 81.

Besedovsky, H., et al., Immunoregulatory feedback between interleukin-1 and glucocorticoid hormones, Science, vol. 233, pp. 652-654, 1986.

Blackwell, T. S. et al., Sepsis and cytokines: current status, Br. J. Anaesth., vol. 77, pp. 110-117, 1996.

Borovikova et al., Acetylcholine inhibition of immune response to bacterial endotoxin in human macrophages, Abstracts, Society for Neuroscience, 29th Annual Meeting, Miami Beach, FL, Oct. 23-28, 1999, Abstract No. 624.6.

Bulloch et al.; Characterization of choline O-acetyltransferase (ChAT) in the BALB/C mouse spleen; Int.J.Neurosci.; 76; pp. 141-149; 1994.

Burke et al., Bent pseudoknots and novel RNA inhibitors of type 1 human immunodeficiency virus (HIV-1) reverse transcriptase, J. Mol. Biol., vol. 264; pp. 650-666, 1996.

Cano et al.; Characterization of the central nervous system innervation of the rat spleen using viral transneuronal tracing; J.Comp Neurol.; 439; pp. 1-18; 2001.

Das, Critical advances in spticemia and septic shock, Critical Care, vol. 4, pp. 290-296, Sep. 7, 2000.

Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.

Ellington et al., In vitro selection of RNA molecules that bind specific ligands, Nature, vol. 346, pp. 818-822, Aug. 30, 1990.
Fox, D. A., Cytokine blockade as a new strategy to treat rheumatoid arthritis, Arch. Intern. Med., vol. 160, pp. 437-444, Feb. 28, 2000.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, 1995.
Ghelardini et al., S-(–)-ET 126: A potent and selective M1 antagonist in vitro and in vivo, Life Sciences, vol. 58, No. 12, pp. 991-1000, 1996.
Goyal et al., Nature of the vagal inhibitory innervation to the lower esophageal sphincter, Journal of Clinical Investigation, vol. 55, pp. 1119-1126, May 1975.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Guslandi, M., Nicotine treatment for ulcerative colitis, Br. J. Clin. Pharmacol., vol. 48, pp. 481-484, 1999.
Harrison's Principles of Internal Medicine, vol. 13, pp. 511-515 and 1433-1435, 1994.
Hirao et al., The limits of specificity: an experimental analysis with RNA aptamers to MS2 coat protein variants, Mol. Divers., vol. 4, pp. 75-89, 1999.
Hsu, et al., Analysis of efficiency of magnetic stimulation, IEEE Trans. Biomed. Eng., vol. 50(11), pp. 1276-1285, Nov. 2003.
Jaeger et al., The structure of HIV-1 reverse transcriptase complexed with an RNA pseudoknot inhibitor, The EMBO Journal, 17(15), pp. 4535-4542, 1998.
Joshi et al., Potent inhibition of human immunodeficiency virus type 1 replection by template analog reverse transcriptase, J. Virol., 76(13), pp. 6545-6557, Jul. 2002.
Kawashima, et al., Extraneuronal cholinergic system in lymphocytes, Pharmacology & Therapeutics, vol. 86, pp. 29-48, 2000.
Kees et al; Via beta-adrenoceptors, stimulation of extrasplenic sympathetic nerve fibers inhibits lipopolysaccharide-induced TNF secretion in perfused rat spleen; J.Neuroimmunol.; 145; pp. 77-85; 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
LeNovere, N. et al., Molecular evolution of the nicotinic acetylcholine receptor: an example of multigene family in excitable cells, J. Mol. Evol., 40, pp. 155-172, 1995.
Leonard, S. et al., Neuronal nicotinic receptors: from structure to function, Nicotine & Tobacco Res. 3:203-223 (2001).
Lips et al.; Coexpression and spatial association of nicotinic acetylcholine receptor subunits alpha7 and alpha10 in rat sympathetic neurons; J.Mol.Neurosci.; 30; pp. 15-16; 2006.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, 1996.
Nagashima et al., Thrombin-activatable fibrinolysis inhibitor (TAFI) deficiency is compatible with murine life, J. Clin. Invest., 109, pp. 101-110, 2002.
Noguchi et al., Increases in Gastric acidity in response to electroacupuncture stimulation of hindlimb of anesthetized rats, Jpn. J. Physiol., 46(1), pp. 53-58, 1996.
Norton, Can ultrasound be used to stimulate nerve tissue, BioMedical Engineering, 2(1), pp. 6, 2003.
Rinner et al.; Rat lymphocytes produce and secrete acetylcholine in dependence of differentiation and activation; J.Neuroimmunol.; 81; pp. 31-37; 1998.
Saindon et al.; Effect of cervical vagotomy on sympathetic nerve responses to peripheral interleukin-1beta; Auton.Neuroscience Basic and Clinical; 87; pp. 243-248; 2001.
Saito, Involvement of muscarinic M1 receptor in the central pathway of the serotonin-induced bezold-jarisch reflex in rats, J. Autonomic Nervous System, vol. 49, pp. 61-68, 1994.
Sandborn, W. J., et al., Transdermal nicotine for mildly to moderately active ulcerative colitis, Ann. Intern. Med, vol. 126, No. 5, pp. 364-371, 1997.
Sato, E., et al., Acetylcholine stimulates alveolar macrophages to release inflammatory cell chemotactic activity, Am. J. Physiol., vol. 274, pp. L970-L979, 1998.
Sato, K.Z., et al., Diversity of mRNA expression for muscarinic acetylcholine receptor subtypes and neuronal nicotinic acetylcholine receptor subunits in human mononuclear leukocytes and leukemic cell lines, Neuroscience Letters, vol. 266, pp. 17-20, 1999.
Schneider et al., High-affinity ssDNA inhibitors of the review transcriptase of type 1 human immunodeficiency virus, Biochemistry, 34(29), pp. 9599-9610, 1995.
Shafer, Genotypic testing for human immunodeficiency virus type 1 drug resistance, Clinical Microbiology Reviews, vol. 15, pp. 247-277, 2002.
Sher, M. E., et al., The influence of cigarette smoking on cytokine levels in patients with inflammatory bowel disease, Inflamm. Bowel Dis., vol. 5, No. 2, pp. 73-78, 1999.
Snyder et al., Correction of hemophilia B in canine and murine models using recombinant adeno-associated viral vectors; Nature Medicine, 5(1), pp. 64-70, Jan. 1999.
Steinlein, New functions for nicotine acetylcholine receptors?, Behavioural Brain Res., vol. 95, pp. 31-35, 1998.
Sternberg, E. M., Perspectives series: cytokines and the brain 'neural-immune interactions in health and disease,' J. Clin. Invest., vol. 100, No. 22, pp. 2641-2647, Dec. 1997.
Sykes, et al., An investigation into the effect and mechanisms of action of nicotine in inflammatory bowel disease, Inflamm. Res., vol. 49, pp. 311-319, 2000.
Toyabe, et al., Identification of nicotinic acetylcholine receptors on lymphocytes in the periphery as well as thymus in mice, Immunology, vol. 92, pp. 201-205, 1997.
Tracey, K. J. et al., Anti-cachectin/TNF monoclonal antibodies prevent septic shock during lethal bacteraemia; Nature, 330: pp. 662-664, 1987.
Tsutsui, H., et al., Pathophysiolocical roles of interleukin-18 in inflammatory liver disease; Immunol. Rev., 174:192-209, 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Dijk, A. P., et al., Transdermal nictotine inhibits interleukin 2 synthesis by mononuclear cells derived from healthy volunteers, Eur. J. Clin. Invest, vol. 28, pp. 664-671, 1998.
Walland et al., Compensation of muscarinic brochial effects of talsaclidine by concomitant sympathetic activation in guinea pigs; European Journal of Pharmacology, vol. 330, pp. 213-219, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183, pp. 27-31, 1995.
Webster's Dictionary, definition of "intrathecal", online version accessed Apr. 21, 2009.
Whaley, K. et al., C2 synthesis by human monocytes is modulated by a nicotinic cholinergic receptor, Nature, vol. 293, pp. 580-582, Oct. 15, 1981.

Faltys et al.; U.S. Appl. No. 12/797,452 entitled "Nerve cuff with pocket for leadness stimulator," filed Jun. 9, 2010.
Hatton et al.; Vagal nerve stimulation: overview and implications for anesthesiologists; Int'l Anesthesia Research Society; vol. 103; No. 5; pp. 1241-1249; Nov. 2006.
Hoffer et al.; Implantable electrical and mechanical interfaces with nerve and muscle; Annals of Biomedical Engineering; vol. 8; pp. 351-360; 1980.
Krarup et al; Conduction studies in peripheral cat nerve using implanted electrodes: I. methods and findings in controls; Muscle & Nerve; vol. 11; pp. 922-932; Sep. 1988.
Loeb et al.; Cuff electrodes for chronic stimulation and recording of peripheral nerve activity; Journal of Neuroscience Methods; vol. 64; pp. 95-103; 1996.
Strojnik et al.; Treatment of drop foot using and implantable peroneal underknee stimulator; Scand. J. Rehab. Med.; vol. 19; pp. 37R43; 1987.
Beliavskaia et al.,"On the effects of prolonged stimulation of the peripheral segment of the vagus nerve on blood clotting time under different bodily conditions," Fiziologicheskii Zhurnal SSSR Imeni I.M. Sechenova., vol. 52(11); p. 1315-1321, Nov. 1966.
Kalishevskaya et al.; Neural regulation of the fluid state of the blood; Usp. Fiziol. Nauk;,vol. 13; No. 2; pp. 93-122; 1982.
Kuznik, et al., "Role of the heart and vessels in regulating blood coagulation and fibrinolysis," Kagdiologiia, vol. 13(4): pp. 145-154, 1973.
Kuznik, "Role of the vascular wall in the process of hemostatis," Usp Sovrem Biol., vol. 75(1): pp. 61-85, 1973.
Pateyuk, et al.,"Treatment of Botkin's disease with heparin," Klin. Med., vol. 51(3): pp. 113-117, 1973.
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Cicala et al., "Linkage between inflammation and coagulation: An update on the molecular basis of the crosstalk," Life Sciences, vol. 62(20); pp. 1817-1824, 1998.
Kalishevskaya et al. "The character of vagotomy-and atropin-induced hypercoagulation," Fizio. Zh SSSR Im I M Sechenova, 65(3): pp. 398-404, 1979.
Khatun, S., et al., "Induction of hypercoagulability condition by chronic localized cold stress in rabbits," Thromb. and Haemost., 81: pp. 449-455, 1999.
Kudrjashov, et al. "Reflex nature of the physiological anticoagulating system," Nature, vol. 196(4855): pp. 647-649; 1962.
Kuznik, et al., "Secretion of blood coagulation factors into saliva under conditions of hypo-and hypercoagulation," Voprosy Meditsinskoi Khimii, vol. 19(1): pp. 54-57; 1973.
Kuznik, et al., "Heart as an efferent regulator of the process of blood coagulation and fibrinolysis," Kardiologiia, vol. 13(3): pp. 10-17, 1973.
Kuznik, et al., "Blood Coagulation in stimulation of the vagus nerve in cats," Biull. Eskp. Biol. Med., vol. 78(7): pp. 7-9, 1974.
Kuznik, et al., "The role of the vascular wall in the mechanism of control of blood coagulation and fibrinolysis on stimulation of the vagus nerve," Cor Vasa, vol. 17(2): pp. 151-158, 1975.
Kuznik, et al., "The dynamics of procoagulatible and fibrinolytic activities during electrical stimulation of peripheral nerves," Fizio. Zh SSSR Im I M Sechenova, 3: pp. 414-420, 1979.
Lang, et al., "Neurogienic control of cerebral blood flow," Experimental Neurology, 43: pp. 143-161, 1974.

Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Mishchenko, et al., "Coagulation of the blood and fibrinolysos in dogs during vagal stimulation," Fizio. Zh SSSR Im I M Sechenova, vol. 61(1): pp. 101-107, 1975.
Von Känal, et al., Effects of sympathetic activation by adrenergic infusions on hemostasis in vivo, Eur. J. Haematol., vol. 65: pp. 357-369, 2000.
Cohen, "The immunopathogenesis of sepsis," vol. 420(19): pp. 885-891, 2002.
Weiner, et al., "Inflammation and therapeutic vaccination in CNS diseases," vol. 420(19): pp. 879-884, 2002.
Benoist, et al., "Mast cells in autoimmune disease" vol. 420(19): pp. 875-878, 2002.
Zitnik et al.; U.S. Appl. No. 12/874,171 entitled "Prescription pad for treatment of inflammatory disorders," filed Sep. 1, 2010.
Faltys et al.; U.S. Appl. No. 12/978,250 entitled "Neural stimulation devices and systems for treatment of chronic inflammation," filed Dec. 23, 2010.
Ben-Noun et al.; Neck circumference as a simple screening measure for identifying overweight and obese patients; Obesity Research; vol. 9; No. 8; pp. 470-477; Aug. 8, 2001.
Bushby et al; Centiles for adult head circumference; Archives of Disease in Childhood; vol. 67; pp. 1286-1287; 1992.
Hansson, E.; Could chronic pain and spread of pain sensation be induced and maintained by glial activation?. Acta Physiologica, vol. 187: pp. 321R327, 2006.
Payne, J. B. et al., Nicotine effects on PGE2 and IL-1 beta release by LPS-treated human monocytes, J. Perio. Res., vol. 31, No. 2, pp. 99-104, 1996.
Pullan, R. D., et al., Transdermal nicotine for active ulceratiive colitis, N. Engl. J. Med., vol. 330, No. 12, pp. 811-815, 1994.
Pulvirenti et al; Drug dependence as a disorder of neural plasticity:focus on dopamine and glutamate; Rev Neurosci.; vol. 12; No. 2; pp. 141-158; 2001.
Suter et al.; Do glial cells control pain?; Neuron Glia Biol.; vol. 3; No. 3; pp. 255-268; Aug. 2007.
Takeuchi et al., A comparision between chinese blended medicine "Shoseiryuto" tranilast and ketotifen on the anit-allergic action in the guinea pigs, Allergy, vol. 34, No. 6, pp. 387-393, 1985 (eng. abstract).
Levine, Jacob A.; U.S. Appl. No. 13/338,185 entitled "Modulation of sirtuins by vagus nerve stimulation" filed Dec. 27, 2011.
Tracey, K. J. et al., Physiology and immunology of the cholinergic antiinflammatory pathway; J Clin Invest.; vol. 117: No. 2; pp. 289-296; Feb. 2007.
Van Der Horst et al.; Stressing the role of FoxO proteins in lifespan and disease; Nat Rev Mol Cell Biol.; vol. 8; No. 6; pp. 440-450; Jun. 2007.
Levine et al.; U.S. Appl. No. 13/467,928 entitled "Single-Pulse Activation of the Cholinergic Anti-Inflammatory Pathway to Treat Chronic Inflammation," filed May 9, 2012.
Nadol et al., "Surgery of the Ear and Temporal Bone," Lippinkott Williams & Wilkins, 2nd Ed., 2005, (Publication date: Sep. 21, 2004), p. 580.
US 6,184,239, 02/2001, Puskas (withdrawn)

* cited by examiner

DEVICES AND METHODS FOR INHIBITING GRANULOCYTE ACTIVATION BY NEURAL STIMULATION

CROSS REFERENCE TO RELATED APPLICATIONS

This application claims benefit to U.S. application Ser. No. 60/968,292 filed on Aug. 27, 2007, entitled, "DEVICES AND METHODS FOR INHIBITING GRANULOCYTE ACTIVATION BY NEURAL STIMULATION."

BACKGROUND OF THE INVENTION

Neutrophils, eosinophils and basophils are known as granulocytes because of their content of cytoplasmic granules, or phagocytes because they may phagocytize or ingest bacteria, microorganisms and other types of foreign materials. These cells are produced from common progenitor cells in the bone marrow of a human or animal, and are known to circulate in peripheral blood and enter tissues as necessary for control of infection or to participate in any type of inflammatory reaction. The neutrophil is the most common leukocyte in human and animal peripheral blood.

In the response to any type of infection or inflammation, granulocytes are activated to migrate to the appropriate area in response to chemoattractant factors, such as, certain bacterial products, complement component, and other factors. This attraction process is termed chemotaxis. Once in an area of inflammation or infection, granulocytes and mononuclear phagocytes must establish a firm attachment to their targets. For this purpose, these cells possess a number of specific cell surface receptor glycoproteins that promote this interaction, such as complement, Fc, and fibronectin receptors.

One family of cell surface receptor glycoproteins is the leukocyte cell adhesion molecular (LEU-CAM) family (CD11/CD18). This family is comprised of cell surface proteins which have multiple subunits. The members of this family include LFA-1 (CD 11a/CD18), Mol (CD 11b/CD18), and P150,94 (CD 11c/CD18).

Activation of granulocytes (and particularly neutrophils) is involved in numerous disorders and diseases, particularly those involving inflammation. While the inflammatory response of granulocytes is vital to the eradication of invading microorganisms, substantial evidence indicates that inflammatory phagocytes cause damage to various organs and tissues when these cells are activated as part of an ongoing (chronic) process, or are triggered in an unregulated manner. The adhesion and spreading of activated granulocytes (e.g., neutrophils) to vascular endothelial cells with the subsequent release of toxic oxidative metabolites and proteases has been implicated in the organ damage observed in diseases or disorders ("granulocyte-mediated disorders") such as adult respiratory distress syndrome (ARDS; shock lung syndrome), glomerulonephritis, and inflammatory injury occurring after reperfusion of ischemic tissue such as to the heart, bowel, and central nervous system, among others. Heart muscle or myocardium may be particularly vulnerable to the inflammatory response of activated granulocytes. For example, it has been suggested that inhibition of the activation of granulocytes prior to cardiac insult (e.g., myocardial ischemia) may result in significantly smaller damage, and reduced myocardial infarct size.

U.S. Pat. No. 4,840,793 to Todd III, et al., as well as related U.S. Pat. No. 4,935,234, U.S. Pat. No. 5,049,659 and U.S. Pat. No. 5,019,648 describe the inhibition of activated granulocytes by administering monoclonal antibodies that inhibit adhesion-dependent functions of glycoproteins such as CD11b to inhibit migration of neutrophils to an area of inflammation or infection. Other groups have used recombinant soluble adhesive receptors as anti-inflammatory compounds. Thus, the majority of treatments for granulocyte-mediated disorders or diseases have been treated by systemically applying exogenous substances that interact with granulocytes that have already undergone activation. It would be highly desirable to more directly inhibit granulocyte activation, as described herein.

SUMMARY OF THE INVENTION

Described herein are methods of inhibiting granulocyte activation and devices and systems for inhibiting granulocyte activation. The methods, devices and systems described herein may inhibit granulocyte activation by appropriate stimulation of the vagus nerve. In particular, neutrophil activation may be inhibited by appropriate vagus nerve stimulation. Cellular activation of granulocytes (including neutrophils) may be detected by the expression of cell-surface receptors such as CD11b or other cellular components that are part of a cellular immunity or inflammation response associated with granulocytes.

The methods and systems described herein may be particularly useful to prevent or treat granulocyte-mediated diseases or disorders. Examples of such disorders and diseases are provided below. In general, granulocyte-mediated diseases or disorders include any disease or disorder in which activated granulocytes cause, enhance or exacerbate a deleterious biological effect, including inflammatory disorders or diseases. This includes all neutrophil-mediated diseases or disorders. For example, diabetes, atherosclerosis, and many cancers are neutrophil-mediated diseases.

In general, a granulocyte-mediated disorder may be prevented and/or treated by stimulating the vagus nerve in an appropriate manner. For example, a method of treating and/or preventing a granulocyte-mediated disease or disorder may include the steps of identifying a subject suffering from, or at risk for, a disease or disorder mediated by granulocyte activation, and stimulating the subject's vagus nerve in an amount sufficient to achieve an inhibition in expression of a marker of granulocyte activation without desensitizing the response of the granulocytes to vagal stimulation.

Appropriate stimulation of the vagus nerve results in an inhibition of granulocyte activation (particularly sustained inhibition of neutrophil activation), without desensitizing the inhibitory pathway by overstimulating the vagus nerve. For example, appropriate stimulation may be extremely low frequency, low level stimulation. Examples of appropriate stimulation are provided below. Appropriately stimulating the vagus nerve may result in a sustained inhibition in granulocyte activation, which can be detected or measured by examining the expression of a marker of granulocyte activation, such as CD11b. In some variations, the stimulation of the subject's vagus nerve results in inhibition of expression of some markers of granulocyte activation (such as cell-surface receptors like CD11b) without substantially inhibiting the expression of other granulocyte proteins. Thus, the subject's vagus nerve may be specifically stimulated to achieve a reduction of expression of a marker of granulocyte activation without substantially reducing the expression of other markers, such as HLA-DR (Ia) and other class II antigens.

The vagus nerve may be stimulated to inhibit granulocyte activation by any appropriate mode of stimulation. In particular, the vagus nerve may be stimulated by electrical stimulation, mechanical stimulation, or electromagnetic stimulation.

These methods of stimulation may be direct or indirect. Indirect stimulation of the vagus nerve may be performed through tissue (e.g., transvascularly, transcutaneously, etc.). A stimulator may be external or implanted, and may be particularly configured to provide the extremely low frequency, low level stimulation described below. In some variations, the stimulator is activated or controlled by feedback from one or more sensors configured to detect activation (e.g., activation level) of granulocytes (e.g., the level or change in level of CD11b on neutrophils).

Mechanical stimulation of the vagus nerve may involve applying pressure to the vagus nerve. For example, mechanical stimulation may be applied by pressing or squeezing the nerve, or a region of tissue including a portion of the vagus nerve. Pressure may be applied externally (e.g., to a region of the body enervated by a branch of the vagus nerve such as the pinna region of the ear), or internally (e.g., from an implant).

In some variations, the method of treating and/or preventing a granulocyte-mediated disorder may include the step of implanting a stimulator for stimulating the vagus nerve. For example, a stimulator may be a transvascular stimulator that is implanted subclavically.

Treatment and/or prevention of a granulocyte-mediated disorder may also involve the step of detecting activated granulocytes, or the activation level of granulocytes. The activation level of granulocytes may be determined by detecting the expression of markers of granulocyte activation, such as the detection (and/or quantification) of a cell-surface marker such as CD11b on neutrophils. Changes in the activation level of granulocytes (such as neutrophils) may be used to control the stimulation of the vagus nerve to inhibit granulocyte activation. Thus, this information may be used to provide feedback to control or regulate stimulation of the vagus nerve to inhibit granulocyte activation. As described in further detail below, the activation level of granulocytes may also be examined to identify or characterize a subject that is a good candidate for vagal stimulation to inhibit granulocyte activation, and therefore a good candidate to receive vagal stimulation to prevent or treat a granulocyte-mediated disease or disorder.

The methods and devices for inhibiting granulocyte activation described herein may be limited to inhibition of one class of granulocytes, such as neutrophils. In some variations, the methods and devices described herein may be selective (or substantially selective) for inhibition of one class of granulocytes over another class of granulocytes. For example, activation of neutrophils may be inhibited preferentially compared to activation of eosinophils. Furthermore, activation of granulocytes or a class of granulocytes may be assayed by any appropriate marker for granulocyte activation, including cell surface receptor glycoproteins such as CD11b. In some variations, the activation of granulocytes refers to the level of surface expression of CD11b.

A granulocyte-mediated disorder or disease may refer to any granulocyte-mediated disorder or disease, particularly inflammatory diseases or disorders in which granulocyte activity has been implicated, and where inhibition of granulocyte activation (e.g., neutrophil activation) may be beneficial. Examples of granulocyte-mediated diseases or disorders include, but are not limited to: diabetes, atherosclerosis, and other inflammatory disorders. In some variations, the granulocyte-mediated disorders are neutrophil-mediated disorders or disorders in which CD11b has been implicated ("CD11b-mediated disorders).

Also described herein are methods of treating and/or preventing a granulocyte-mediated disease or disorder in a subject that include the step of stimulating the subject's vagus nerve in an amount sufficient to inhibit the expression of CD11b on the surface of the subject's granulocyte cells without desensitizing the response of the granulocytes to vagal stimulation. In some variations, the stimulation of the subject's vagus nerve is sufficient to inhibit CD11b expression for longer than an extended period time, such as greater than 12 hours, greater than 24 hours, greater than 36 hours, etc.

As mentioned, any appropriate vagal stimulation may be used, including mechanical stimulation, electrical stimulation, and/or electromagnetic stimulation. In particular, the stimulation may be extremely low frequency, low level stimulation. For example, the vagus nerve may be stimulated mechanically by a pulse of light vibration energy (e.g., between 0.1 and 400 Hz (e.g., between 0.1 Hz and 200 Hz, between 0.1 and 100 Hz, between 0.1 and 60 Hz, between 0.1 and 30 Hz, between 0.1 and 10 Hz, between 0.1 and 1 Hz, etc.), applied for between about 30 minutes and about 30 second (e.g., between about 20 minutes and about 30 seconds, between about 10 minutes and 30 seconds, between about 5 minutes and 1 minute, etc.). A pulse of stimulation may then be followed by a quiescent (unstimulated) time period of between about 2 hours and about 72 hours. For example, the quiescent time period may be approximately 12 hours, 24 hours, 36 hours, 48 hours, etc. It may be preferably to tailor the quiescent time period to the actual level of granulocyte activation. Similarly, electrical or electromagnetic stimulation may also be performed. For example, electrical stimulation may be very light (e.g., less than 100 mV, less than 10 mV, less than 1 mV, etc.) at an inter-stimulus frequency of between 0.1 Hz and 200 Hz, between 0.1 and 100 Hz, between 0.1 and 60 Hz, between 0.1 and 30 Hz, between 0.1 and 10 Hz, between 0.1 and 1 Hz, etc.), applied for between about 30 minutes and about 30 second (e.g., between about 20 minutes and about 30 seconds, between about 10 minutes and 30 seconds, between about 5 minutes and 1 minute, etc.). A pulse of stimulation may then be followed by a quiescent (unstimulated) time period of between about 2 hours and about 72 hours. Any appropriate stimulation intensity, duration, inter-stimulus frequency, and quiescent period may be used. Light intensity and low-frequency stimulation is particularly useful.

As mentioned briefly above, stimulation of the vagus nerve may also be controlled or coordinated with detection of granulocyte activation. Also described herein are methods for treating and/or preventing a granulocyte-mediated disease or disorder in a subject in which granulocyte activation is measured. These methods may include the step of detecting a granulocyte activation level and applying stimulation to the subject's vagus nerve to inhibit granulocyte activation in response to the detected granulocyte activation level. These methods may use feedback to control activation of vagus nerve to inhibit granulocyte activation. For example, in some variations the method also includes detecting a second granulocyte activation level and applying a second stimulation to the subject's vagus nerve in response to the second subject's vagus level.

The step of detecting a granulocyte activation level may involve the detection of expression of CD11b expression on granulocytes. As mentioned above, stimulation may include mechanical stimulation, electrical stimulation, and/or electromagnetic stimulation.

Also described herein are systems for treating or preventing a granulocyte-mediated disease or disorder in a subject. These systems may include a sensor to detect granulocyte activation level and a stimulator for stimulating a vagus nerve in response to the detected granulocyte activation level. For example, the sensor may be configured to determine CD11b expression on granulocyte cells. The stimulator may be configured to stimulate the vagus nerve in an amount sufficient to inhibit granulocyte activation without desensitizing the response of the granulocytes to vagal stimulation.

Also described herein are systems to treat or prevent a granulocyte-mediated disease or disorder in a subject. The system may include a sensor to detect CD11b expression on neutrophils, and a stimulator for mechanically stimulating a vagus nerve in response to the level of CD11b expression, whereby the neutrophil activation is inhibited.

INCORPORATION BY REFERENCE

All publications and patent applications mentioned in this specification are herein incorporated by reference in their entirety as if each individual publication or patent application was specifically and individually indicated to be incorporated by reference.

BRIEF DESCRIPTION OF THE DRAWINGS

A better understanding of the features and advantages of the present invention will be obtained by reference to the following drawings.

DETAILED DESCRIPTION OF THE INVENTION

Figure 1:
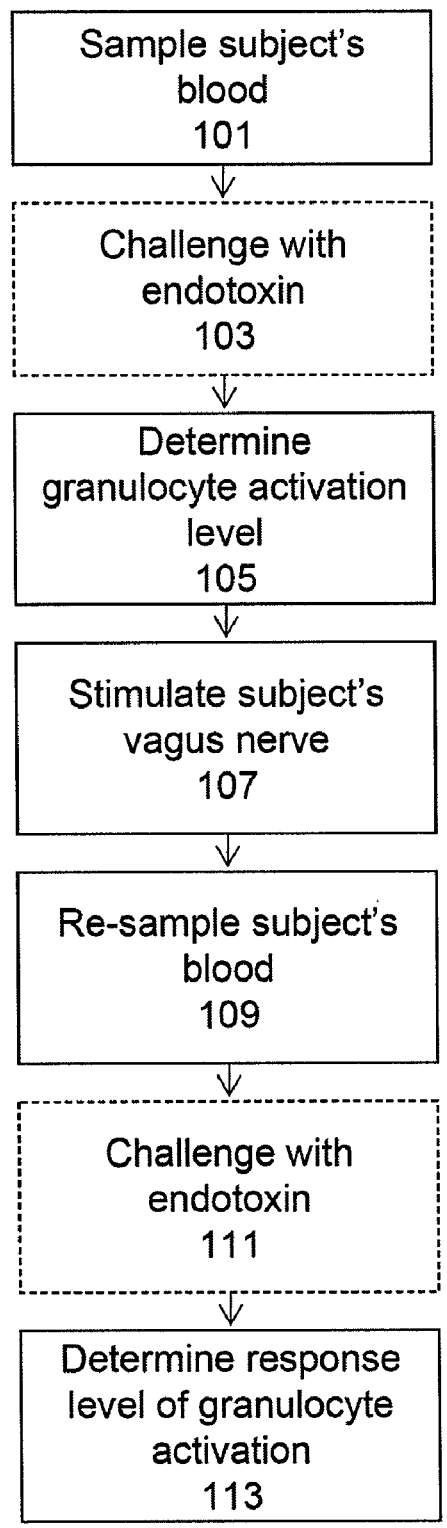
FIG. 1 illustrates one variation of a method of screening a subject to determine the subject's response to inhibition of granulocyte activation by vagal stimulation.

The methods, devices and systems described herein originate from the surprising observation that granulocyte activation may be inhibited by appropriate stimulation of the inflammatory reflex, which includes the vagus nerve. Thus, granulocyte-mediated disorders and diseases may be prevented, treated and/or lessened by appropriately stimulating the inflammatory reflex. This basic observation is described below, followed by a discussion and illustrations of the types of stimulation that are appropriate for inhibiting granulocyte activation. A description of some of the applications of vagal stimulation to inhibit granulocyte activation is also described, including variations of devices, systems and methods of treatment. Specific examples of inhibition of granulocyte activation are also provided. Although the examples and description refer to stimulation of the vagus nerve, it should be understood that the same effect described in the methods, devices and systems herein may be achieved by appropriate stimulation of other portions of the inflammatory reflex. The Vagus nerve is part of an inflammatory reflex, which also includes the splenic nerve, the hepatic nerve and the trigeminal nerve. The efferent arm of the inflammatory reflex may be referred to as the cholinergic anti-inflammatory pathway. For example, Tracey et. al., have previously reported that the nervous system regulates systemic inflammation through a Vagus nerve pathway. This pathway may involve the regulation of inflammatory cytokines and/or activation of granulocytes. Thus, it is believed that appropriate modulation of the Vagus nerve may help regulate inflammation.

As used herein, the term "vagus nerve" may refer to any cranial nerve X, including the main nerve, and any nerves that branch off of the main vagus nerve, as well as ganglionic or post-ganglionic neurons connected to the vagus nerve. The vagus nerve may be referred to as a cholinergic nerve, and may include both afferent and efferent nerve fibers. The term "stimulation" in reference to the vagus nerve is described in greater detail below, but may include any appropriate type of stimulation, including mechanical, electrical, electromagnetic, etc. Stimulation may be direct, e.g., via contact with a portion of the vagus nerve (e.g., by electrode) or indirect, through one or more adjacent tissues or barriers (including external stimulation from outside of the body). A patient (or subject) may include any mammal, preferably a human, but may include domestic, farm, laboratory, or wild animals.

As mentioned above, a granulocyte typically refers to a neutrophil, esinophil or basophil. In some of the variations described herein, the "granulocytes" referred to are neutrophils. In other variations, a granulocyte may refer to any of neutrophil, eosinophil, or basophil. A granulocyte may transform from an un-activated granulocyte into an activated granulocyte (e.g., an activated neutrophil). Once activated, granulocytes can migrate into tissue, and/or move to a specific body region via chemotaxis.

A granulocyte-mediated disease or disorder may include any disease or disorder in which activated granulocytes cause, enhance or exacerbate a deleterious biological effect, including inflammatory disorders or diseases. Granulocyte-mediated diseases or disorders include neutrophil-mediated diseases or disorders. Non-limiting examples of granulocyte-mediated diseases or disorders include: diabetes, atherosclerosis, many cancers, septic shock, acute respiratory distress syndrome (ARDS), bacterial meningitis, acute pancreatitis, multiple organ failure (MOF), post-ischemic reperfusion, acute cellulitis, abdominal aortic aneurysm, asthma, osteomyelitis, Crohn's disease, cystic fibrosis, emphysema, septic or bacterial pyelonephritis, rheumatoid arthritis, septic arthritis, uveitis, periodontitis, psoriasis, severe burns, skin ulceration, acute lung injury, pneumonia, trauma, severe early graft dysfunction, brochioeactasis, chronic obstructive pulmonary disease (COPD), complications with hemodialysis, hypersensitivity pneumonitis, lung fibrosis, herpes stromal keratitis, vascular restenosis, glomerulonephritis, hypersensitivity, cardiac rupture arising as a complication of myocardial infarction, multiple sclerosis, stroke and cerebral ischemia, and traumatic brain injury.

1. Basic Observation

Granulocyte activation may be inhibited by appropriate stimulation of the vagus nerve. In particular, stimulation of the vagus nerve at low intensity and low frequency may result in an inhibition of granulocyte activation following the appropriate stimulation. For example, endotoxin added to blood taken from a subject prior to stimulation of the subject's vagus nerve results in activation of granulocytes, particularly neutrophils. Endotoxin added to blood taken from a subject after external mechanical stimulation of the subject's vagus nerve (as described in Example 1, below) shows a much lower level of granulocyte activation. As described, below, the level of granulocyte activation may be determined by the detection of CD11b on surface of granulocytes.

Furthermore, markers of granulocyte activation such as CD11b are altered by the appropriate stimulation of the vagus nerve, while other markers (such as HLA-DR) are not substantially altered by this stimulation. Although not wishing to be bound by theory, the vagal stimulation may be acting through the spleen to effect activation of granulocytes. The spleen is enervated by the vagus nerve, and typically receives approximately 20% of cardiac output per minute, including circulating granulocytes. Thus, virtually all of the circulating granulocytes pass through the spleen every five minutes. The vagus nerve may therefore signal the spleen to control activation of the granulocytes.

2. Stimulation

In general, appropriate vagus nerve stimulation that may be applied to inhibit granulocyte activation is extremely low frequency, low level stimulation. The range of appropriate stimulation parameters may depend on the particular stimulation modality (e.g., mechanical, electrical, electromagnetic, etc.) that is used, as well as the location of the stimulation (e.g., external, internal, etc.). For example, when electrically stimulating the vagus nerve to inhibit granulocyte activation, very low-intensity (e.g., less than 1V, less than 100 mV, less than 10 mV, less than 1 mV, less than 0.1 mV, less than 0.001 mV) may be used. Similarly, when mechanically stimulating the vagus nerve, a light touch or light pressure on the vagus nerve may be used. For example, the vagus nerve may be stimulated mechanically by a pulse of light vibration energy (e.g., between 0.1 and 400 Hz (e.g., between 0.1 Hz and 200 Hz, between 0.1 and 100 Hz, between 0.1 and 60 Hz, between 0.1 and 30 Hz, between 0.1 and 10 Hz, between 0.1 and 1 Hz, etc.), applied for between about 30 minutes and about 30 second (e.g., between about 20 minutes and about 30 seconds, between about 10 minutes and 30 seconds, between about 5 minutes and 1 minute, etc.). A pulse of stimulation may then be followed by a quiescent (unstimulated) time period of between about 2 hours and about 72 hours. For example, the quiescent time period may be approximately 12 hours, 24 hours, 36 hours, 48 hours, etc. It may be preferably to tailor the quiescent time period to the actual level of granulocyte activation. Similarly, electrical or electromagnetic stimulation may also be performed. For example, electrical stimulation may be very light (e.g., less than 100 mV, less than 10 mV, less than 1 mV, etc.) at an inter-stimulus frequency of between 0.1 Hz and 200 Hz, between 0.1 and 100 Hz, between 0.1 and 60 Hz, between 0.1 and 30 Hz, between 0.1 and 10 Hz, between 0.1 and 1 Hz, etc.), applied for between about 30 minutes and about 30 second (e.g., between about 20 minutes and about 30 seconds, between about 10 minutes and 30 seconds, between about 5 minutes and 1 minute, etc.). A pulse of stimulation may then be followed by a quiescent (unstimulated) time period of between about 2 hours and about 72 hours. Any appropriate stimulation intensity, duration, inter-stimulus frequency, and quiescent period may be used. Light intensity and low-frequency stimulation is particularly useful.

Implantable stimulator may be useful for appropriate stimulation of the vagus nerve to inhibit activation of granulocytes. In particular, non-contact stimulation devices may be useful. A non-contact stimulation device includes an output (e.g., an electrode or transducer) to stimulate the vagus nerve from some distance, such as outside of the nerve sheath. Since even light pressure (touch) to the vagus nerve may stimulate the vagus nerve as described herein, controlled stimulation may require the use of non-contact electrodes that do not apply pressure to the vagus nerve when the patient moves, for example.

Low-intensity or low levels of vagus stimulation may prevent desensitization of the inhibitory effect of vagus nerve stimulation. For example, traditional stimulation of the vagus nerve to drive cardiac pacing, to control seizures, to effect neuropsychological effects, and to treat gastrointestinal and eating disorders typically involves high-intensity and/or high frequency stimulation. Stimulation at these high levels is believed to overdrive the vagus nerve and may desensitize the ability of the granulocytes to respond to vagus stimulation. Desensitization or tachyphylaxis may prevent the sustained inhibition of granulocyte activation that is otherwise possible with the low level vagal stimulation described herein. For example, stimulating at an appropriate low level, may result in sustained inhibition of granulocyte activation for hours or days (e.g., 8 hours, 12, hours, 24 hours, 48 hours, etc.).

3. Applications

A stimulator may be configured to apply the low level of stimulation appropriate for inhibiting granulocyte activation. For example, an electrical stimulator may include one or more non-contact electrodes for placing near a subject's vagus nerve. In some variations, the non-contact electrode of the stimulator may be positioned near any region of the vagus nerve to inhibit granulocyte activation. For example, the electrode(s) may be transvascular electrodes that are placed subcalavicularly. In some variations, the electrodes are implanted behind a subject's ear or in other body regions. The entire stimulator may be implanted, or just the electrode(s) or transducer(s) may be implanted. For example, a mechanical stimulator may include a vibratory element (e.g., a piezoelectric transducer, a shape-memory element, etc.) that can apply pressure to the vagus nerve. The electrode or vibratory element may be connected (via wires or wirelessly) to the rest of the stimulator, which may include a power source and controller for controlling the application of the stimulus. The stimulator controller may be configured to apply the appropriate low-level of stimulation described above.

Figure 3:
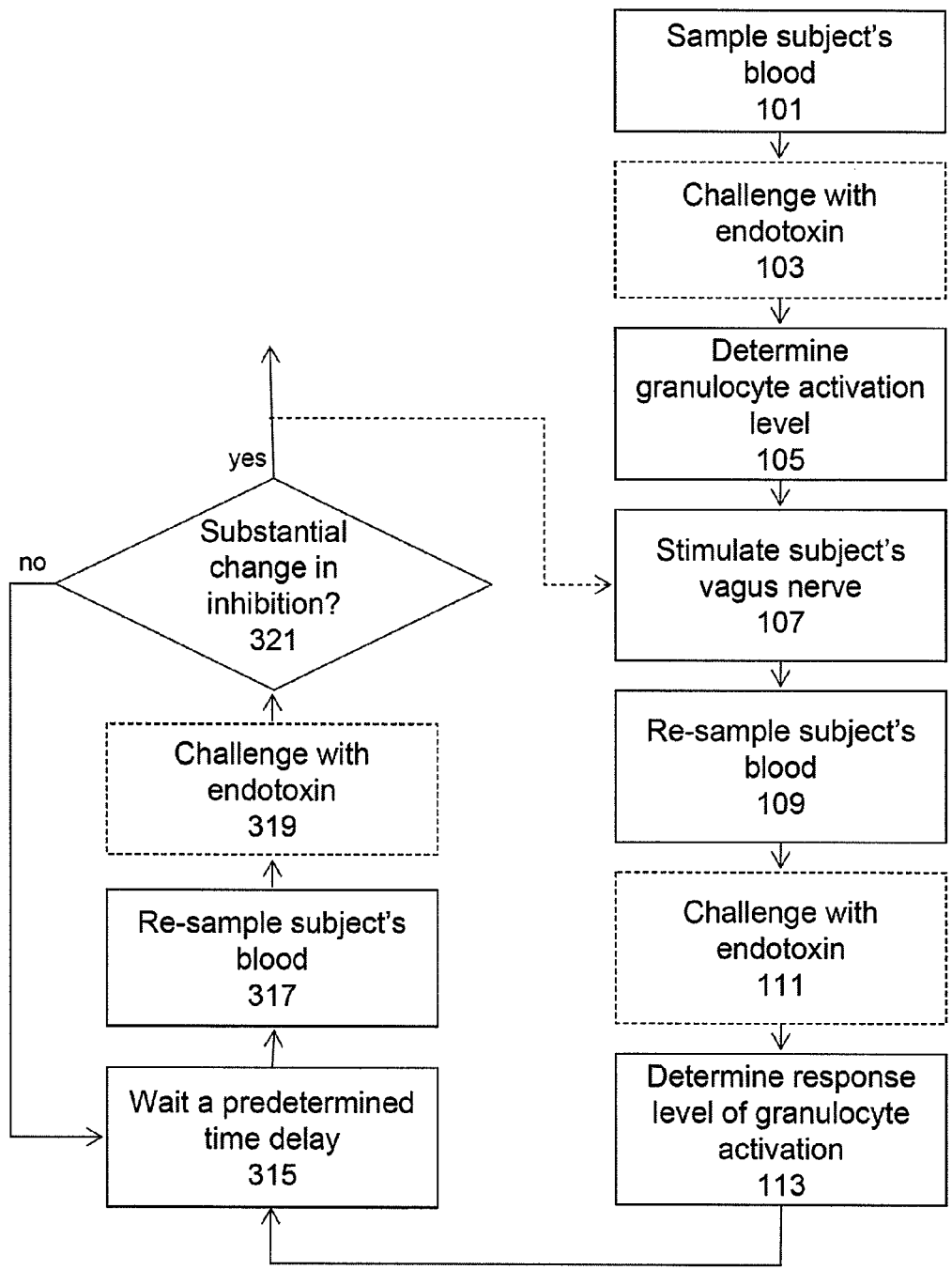
FIG. 3 illustrates one variation of a method for stimulating the vagus nerve of a subject to inhibit granulocyte activation.

In some variations, the stimulator receives feedback from one or more sensors. In particular, sensors for determining the activation level of granulocytes may be useful to provide to help control stimulation. Thus, a method of inhibiting granulocyte activation or of treating a disease or disorder by inhibiting granulocyte activation may include a step of determining the activation level of the granulocytes. FIG. 3, described below, shows one variation of a method using such feedback.

Any appropriate sensor may be used. For example, a sensor may be specific to detecting presence or levels of one or more markers of granulocyte activation. In one example, a sensor determines the level of expression of a glycoprotein receptor on the surface of the granulocytes, such as CD11b.

A system for inhibiting activation of granulocytes may include a stimulator configured to apply the appropriate level of stimulation and a sensor configured to detect a level of granulocyte activation. For example, a system may include a sensor for sensing the level of CD11b on neutrophils in the subject's blood, and a stimulator configured to stimulate at the appropriate low-level to inhibit activation of neutrophils without desensitizing the response. In some variations, a system for inhibiting activation of granulocytes may also include a controller for receiving information from the sensor, analyze the sensed information, and provide feedback (including instructions) to the stimulator.

A sensor and stimulator may also be used to determine if a subject is responsive to stimulation of the vagus to prevent and/or treat a granulocyte-mediated disease or disorder. Individual subjects may respond differently to stimulation of their vagus nerve. The subject may be tested to determine if they are responsive to vagal stimulation to inhibit granulocyte activation, and would benefit from this treatment. Thus, we described herein methods and systems for determining if a subject is a good candidate for inhibition of granulocyte activation by vagal stimulation.

FIG. 1 illustrates one method of screening a subject to determine the subject's response to inhibition of granulocyte activation by vagal stimulation. In the first step 101, the subject's blood is sampled, and then a baseline granulocyte activation level 105 is determined. Optionally, the blood may be challenged with endotoxin 103 prior to determining the activation level. The subject's vagus nerve may then be stimulated 107 (per any of the stimulation methods and protocols described above.), and the blood is again sampled 109 and the activation level determined 113 (optionally, the blood sample may be challenged with endotoxin 111 first, as in step 103). A response level of granulocyte activation can be measured from this second sample. The first and second levels of granulocyte activation can be compared to determine the robustness of the effect (e.g., inhibition of granulocyte activation). In some variations, different markers may be tested, including markers such as CD11b that are typically responsive to vagal stimulation, as well as markers that are not typically responsive.

A system for determining the subject's responsiveness to vagal stimulation and inhibition of granulocyte activation may include stimulation analysis logic for receiving simulation sensor input and stimulation protocols. Thus, this system may include hardware, software or some combination thereof to receive and analyze the subject's granulocyte activation response. For example, a system may include a microcomputer or other processor, including memory, configured to receive and analyze sensor data and data to/from the stimulator. In some variations, the system includes an output (e.g., a monitor or telemetry) for presenting information (including the data) about the subject's response.

Figure 2:
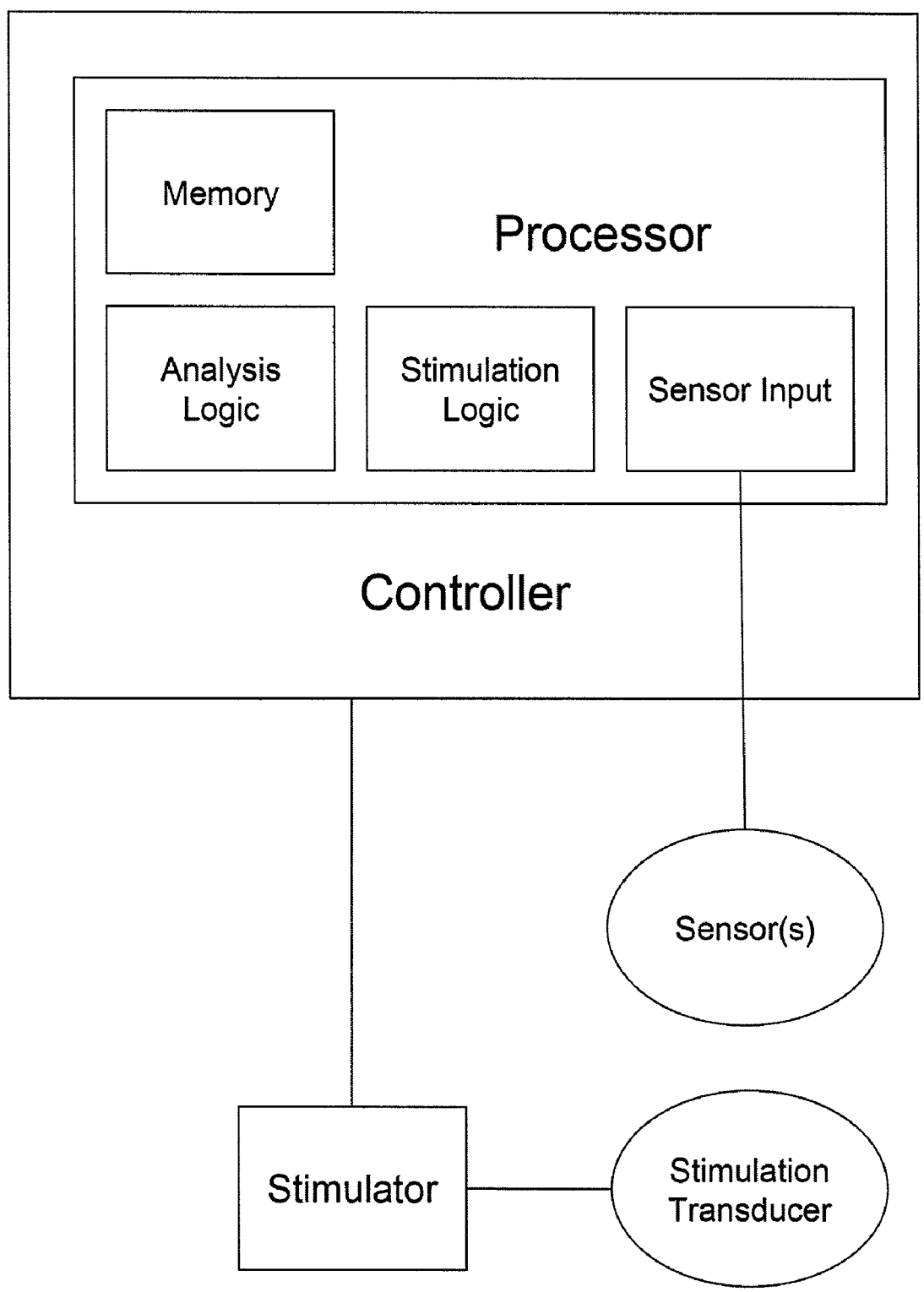
FIG. 2 is a schematic illustration of a system for stimulating the vagus nerve to inhibit granulocyte activation.

In one exemplary system (such as the system shown schematically in FIG. 2) a subject may be implanted with a vagus nerve stimulator, as described above. The vagus nerve stimulator may include a transducer (e.g., electrode, force applicator, etc.) for applying stimulation to the vagus nerve (either directly or indirectly). The transducer may be connected wirelessly or may be wired to the rest of the stimulation. The stimulator may also communicate with a stimulator controller that controls the application of stimulation. Communication between the stimulator and the controller may be wireless or wired. The controller may include a processor, and may also receive information from one or more sensors. The processor may include a memory, and either or both analysis logic (competent to analyze the sensor data) and stimulation logic (to help in controlling the stimulator).

A subject may also be screened to determine the level and/or frequency of stimulation to inhibit granulocyte activation without desensitizing the response of the granulocytes to vagal stimulation. FIG. 3 schematically illustrates a modification of the method of FIG. 1 that may be used to optimize stimulation applied to the vagus nerve to inhibit granulocyte activation without desensitizing. In FIG. 3, the vagus nerve is initially stimulated 107 as described above, and a response level for inhibition may be determined 113. After a predetermine period of time 315 the subject's blood can be sampled 317 and the activation level of granulocytes determined to see if they are still inhibited (or to what extent it is still inhibited) 321. Optionally, the blood sample may be challenged with endotoxin 319 as previously mentioned for steps 103 and 111. Challenging with endotoxin may magnify or otherwise help resolve the activation level of the granulocytes. If the inhibition of granulocytes has worn off, or if normal granulocyte activation has returned to some threshold level, the vagus nerve may be again stimulated, repeating the process. Any appropriate threshold (e.g., 50%, 70%, 80%, 90%, 100%) may be used. A system such as the system illustrated in FIG. 2 may be used to implement this method.

4. Example

Inhibition of CD11b Expression by Mechanical Stimulation of Vagus

FIGS. 4-7 illustrate the inhibition of granulocyte activation by stimulating the Auricular branch of a subject's vagus nerve. Surprisingly, robust inhibition of the granulocyte activation was seen after only very brief, low intensity stimulation of the subject's vagus nerve. Stimulation was indirect, mechanical stimulation applied externally.

In this example, level of granulocyte (e.g., neutrophil) activation was determined by assaying CD11b or CD16b level at differ times following stimulation. The stimulation applied was mechanical stimulation, consisting of a relatively soft vibration to the external cymba choncha of the subject's ear (right ear). Stimulation was applied for between one minute and five minutes (e.g., one minute in some tests and five minutes in other tests). The frequency of the vibration during the one minute period was between 200 Hz and 0.1 Hz (e.g., 10 Hz). Following the application of stimulation, the subject was not stimulated again. The neutrophil activation was assayed before activation, twenty minutes after activation, sixty minutes after activation and twenty-four hours after activation. Activation was assayed by immunoreactivity from sampled blood. For example, blood samples were put into Lithium heparin tubes. The vagus nerve was stimulated 15 min after baseline blood draw. The subject shown in FIGS. 4-7 was stimulated for one minute (vagus nerve stimulation or "VNS").

At various times after stimulation (e.g., 20 min, 60 min, and 24 hr), blood was collected and sampled. Blood was kept at room temperature and stained for reactivity with anti-CD11b or CD16b antibody on day 2. Staining was performed by first mixing the blood with RPMI (gently). For each time point, 450 µl of blood was aliquoted into two separate FACS tubes (A and B). RPMI media (45 µl) was added to Tube A, and LPS (45 µl, 500 ng/ml, for a final 50 ng/ml) was added to Tube B. Thus, Tube B is the endotoxin-stimulated (or challenged) sample. The tubes are then incubated at 37 C in 5% $CO_2$ for 30 min, then placed on ice. For each sample, 100 µl of blood is aliquoted into FACS tubes containing 18 µl antibody (prepared and set on ice). Controls without antibody, and isotype controls were also performed.

After gently mixing the samples, they were incubated for 60 min at 4° C. (in the dark), and transferred to room temperature conditions where 2.5 ml RBC lysis solution was added, the cells vortexed, and let sit 5-6 min. After an addition vortexing, the cells were again allowed to sit 5-6 min (at room temp), and then centrifuged (1200 rpm for 5-7 min). Cells were then aspirated, washed with PBS (twice), and again aspirated and resuspended in 350 ul PBS, and fixed by adding fixative.

Samples were then 'read' using a flow cytometer (e.g., BD FacsCalibur™). Gating was on 'neutrophils' using FSC vs. SSC and CD16b+. Total mean fluorescence intensity (MFI) for each sample was measured, and background of isotype control was subtracted (if necessary).

Figure 4:
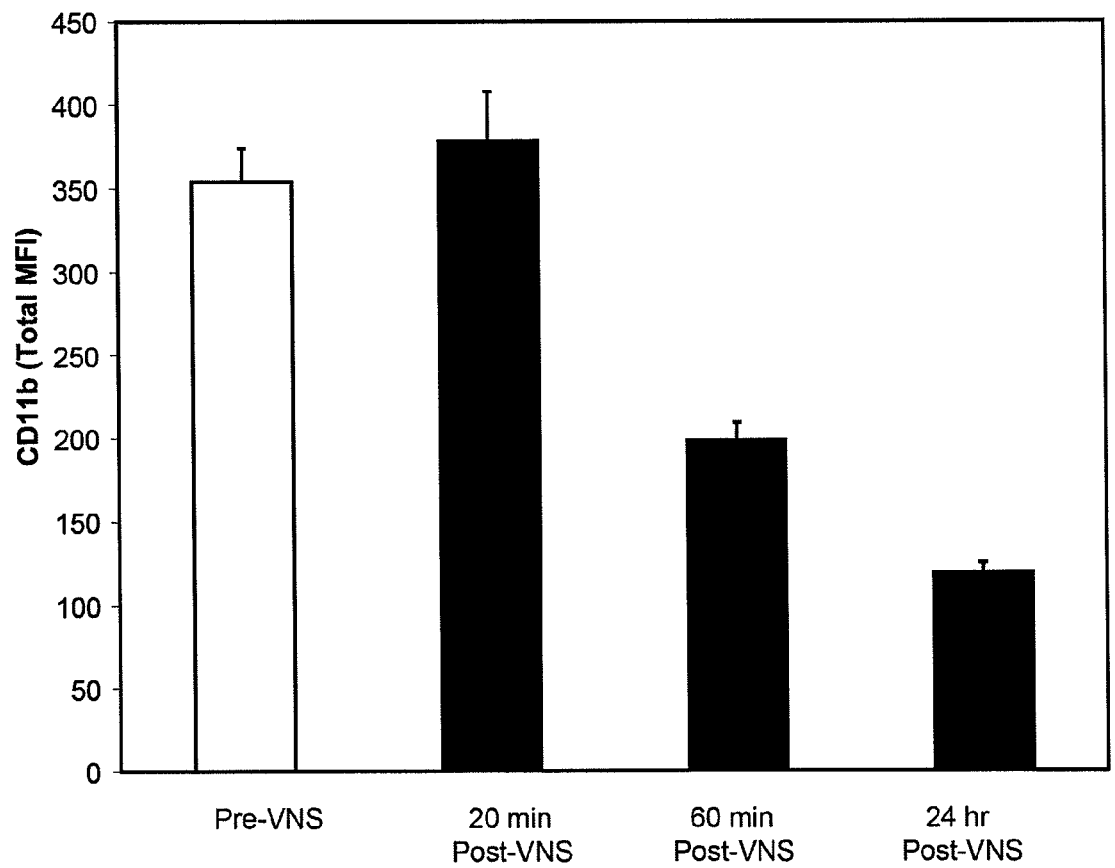
FIG. 4 is a graph showing the effect of VNS on total (neutrophil) CD11b expression in one subject in the LPS unchallenged situation.
Figure 5:
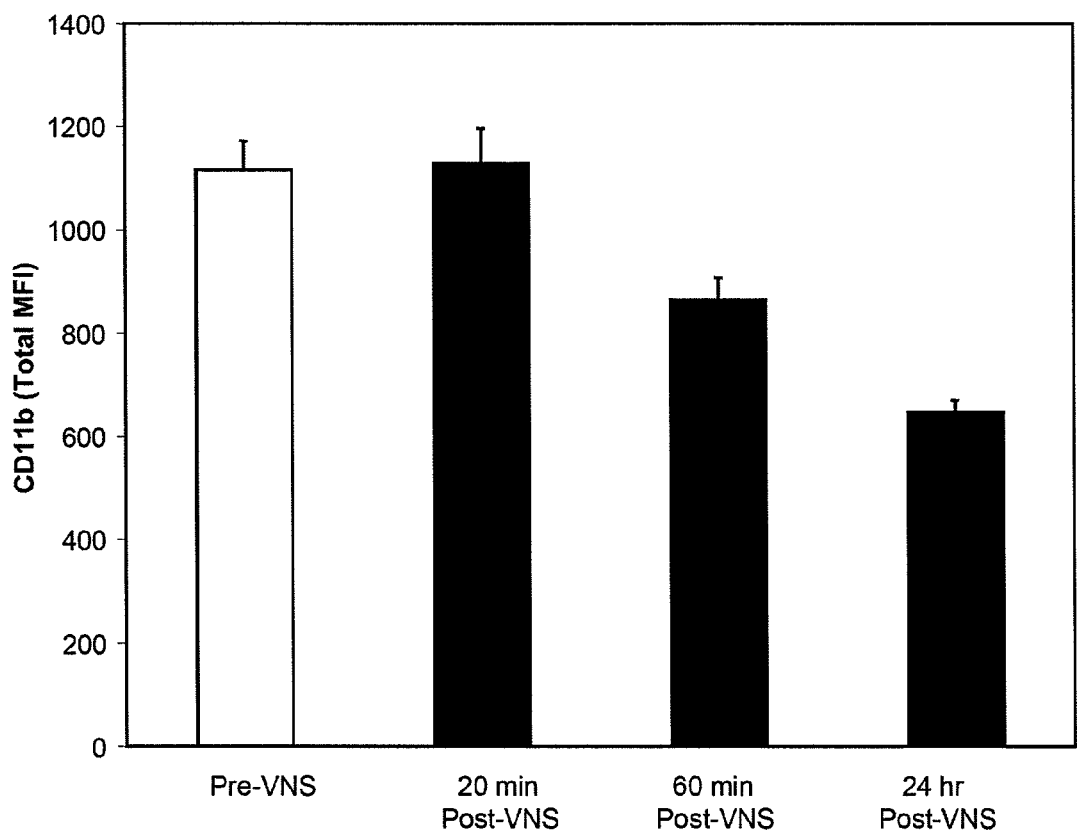
FIG. 5 is a graph showing the effect of VNS on total (neutrophil) CD11b expression in one subject in the LPS challenged situation.

The effect of VNS on total (neutrophil) CD11b expression in one subject is shown in FIGS. 4 and 5 in both the LPS unchallenged (FIG. 4) and challenged (FIG. 5) situations, respectively. In this subject there was very little difference in activation level of neutrophils twenty minutes after stimulation. Thus, the total mean florescence intensity (MFI) of immunolabeled CD11b twenty minutes after stimulation was approximately the same as the MFI of CD11b immediately prior to stimulation (clear bar). After one hour post-VNS, the activation level of the neutrophils, as reflected by the intensity of CD11b staining, begin to fall, an inhibition that was sustained over at least the first twenty-four hours post-VNS. In cells that were challenged with endotoxin (LPS-challenged), the same trend of activation was seen. As expected, the level of CD11b was greatly increased in LPS-challenged cells, as reflected by the CD11b total MFI.

Figure 6:
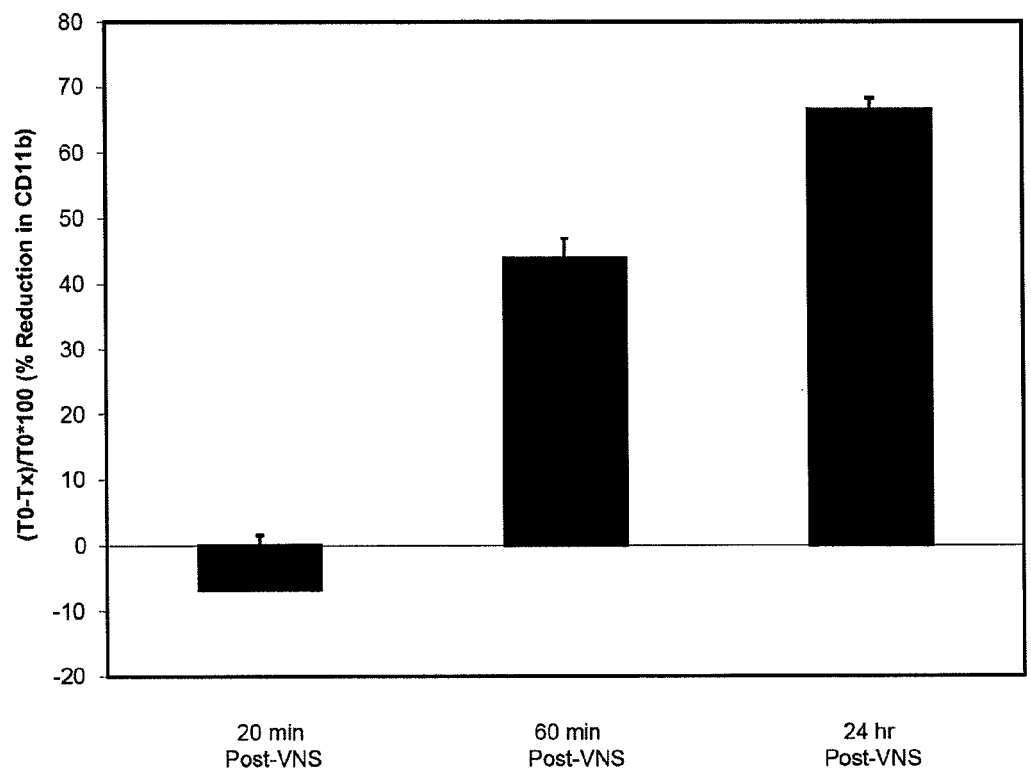
FIG. 6. is a bar graph of the percent reduction in neutrophil CD11b expression (and thus granulocyte activation) in one subject following VNS in the LPS unchallenged situation, compared to immediately before stimulation.
Figure 7:
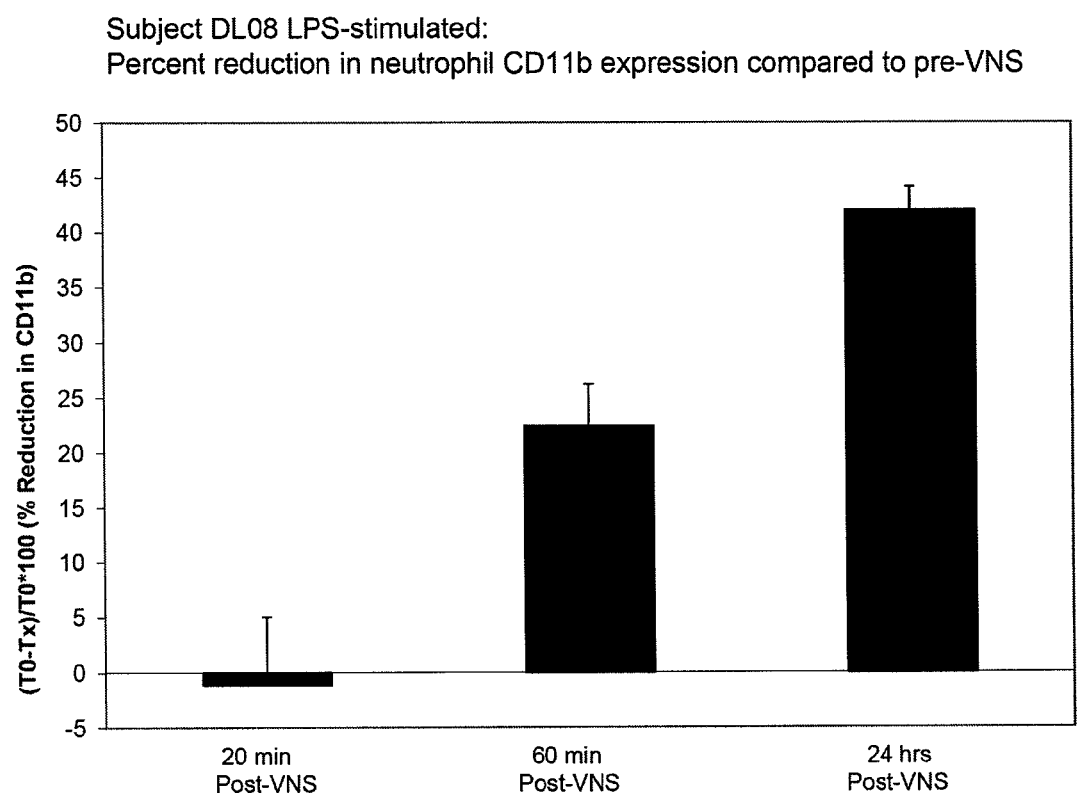
FIG. 7 is a bar graph of the percent reduction in neutrophil CD11b expression (and thus granulocyte activation) in one subject following VNS in the LPS challenged situation, compared to immediately before stimulation.

FIGS. 6 and 7 show the percent reduction in neutrophil CD11b expression (and thus granulocyte activation) in one subject following VNS, compared to immediately before stimulation. Although this subject showed little inhibition shortly after VNS (e.g., at 20 min), a profound, long-lasting inhibition (e.g., beyond 24 hours) developed thereafter, without addition stimulation. From previous experimental data, it is known that overstimulating the Vagus nerve (including mechanically overstimulation), may reduce or eliminate this long-lasting inhibition of granulocyte activation.

While the methods and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. A method of treating and/or preventing a granulocyte-mediated disease or disorder in a subject, the method comprising:
   detecting a granulocyte activation level; and
   stimulating the subject's inflammatory reflex in an amount sufficient to achieve an inhibition in expression of a marker of granulocyte activation without desensitizing the response of the subject's granulocytes to vagal stimulation.

2. The method of claim 1, further comprising stimulating the subject's inflammatory reflex to achieve a sustained reduction of expression of the marker of granulocyte activation.

3. The method of claim 1, further comprising stimulating the subject's inflammatory reflex to achieve a reduction of expression of the marker of granulocyte activation without substantially reducing the expression of CD16b.

4. The method of claim 1, wherein the marker of granulocyte activation is CD11b expression.

5. The method of claim 1, wherein the granulocytes affected by stimulation of the inflammatory reflex are neutrophils.

6. The method of claim 1, wherein the granulocyte-mediated disease or disorder granulocyte is selected from the group consisting of: diabetes, atherosclerosis, cancer, septic shock, acute respiratory distress syndrome (ARDS), bacterial meningitis, acute pancreatitis, multiple organ failure (MOF), post-ischemic reperfusion, acute cellulitis, abdominal aortic aneurysm, asthma, osteomyelitis, Crohn's disease, cystic fibrosis, emphysema, septic or bacterial pyelonephritis, rheumatoid arthritis, septic arthritis, uveitis, periodontitis, psoriasis, severe burns, skin ulceration, acute lung injury, pneumonia, trauma, severe early graft dysfunction, brochioeactasis, chronic obstructive pulmonary disease (COPD), complications with hemodialysis, hypersensitivity pneumonitis, lung fibrosis, herpes stromal keratitis, vascular restenosis, glomerulonephritis, hypersensitivity, cardiac rupture arising as a complication with myocardial infarction, multiple sclerosis, stroke or cerebral ischemia, and traumatic brain injury.

7. The method of claim 1, wherein the inflammatory reflex is stimulated by electrical stimulation.

8. The method of claim 1, wherein the inflammatory reflex is stimulated by mechanical stimulation.

9. The method of claim 1, wherein the inflammatory reflex is stimulated by electromagnetic stimulation.

10. The method of claim 1, wherein the stimulation comprises extremely low frequency, low level stimulation.

11. The method of claim 1, further comprising implanting a stimulator for stimulating the inflammatory reflex.

12. The method of claim 1, further comprising determining if the subject is a candidate for inhibition of granulocyte-mediated disease or disorder by stimulation of the inflammatory reflex.

13. The method of claim 1, wherein the step of stimulating the inflammatory reflex comprises stimulating the vagus nerve.

14. A method of treating and/or preventing a granulocyte-mediated disease or disorder in a subject, the method comprising:
   stimulating the subject's vagus nerve in an amount sufficient to inhibit the expression of CD11b on the surface of the subject's granulocyte cells without desensitizing the response of the granulocytes to vagal stimulation; and
   screening the subject at different times to determine the extent of inhibition of granulocyte activation in response to vagal stimulation.

15. The method of claim 14, wherein the stimulation of the subject's vagus nerve is sufficient to inhibit CD11b expression for a period of greater than 12 hours.

16. The method of claim 14, wherein the disease or disorder is selected from the group consisting of: diabetes, atherosclerosis, cancer, septic shock, acute respiratory distress syndrome (ARDS), bacterial meningitis, acute pancreatitis, multiple organ failure (MOF), post-ischemic reperfusion, acute cellulitis, abdominal aortic aneurysm, asthma, osteomyelitis, Crohn's disease, cystic fibrosis, emphysema, septic or bacterial pyelonephritis, rheumatoid arthritis, septic arthritis, uveitis, periodontitis, psoriasis, severe burns, skin ulceration, acute lung injury, pneumonia, trauma, severe early graft dysfunction, brochioeactasis, chronic obstructive pulmonary disease (COPD), complications with hemodialysis, hypersensitivity pneumonitis, lung fibrosis, herpes stromal keratitis, vascular restenosis, glomerulonephritis, hypersensitivity, cardiac rupture arising as a complication with myocardial infarction, multiple sclerosis, stroke or cerebral ischemia, and traumatic brain injury.

17. The method of claim 14, wherein the stimulation is mechanical stimulation, electrical stimulation, or electromagnetic stimulation.

18. The method of claim 14, wherein the stimulation comprises pressure applied to the subject's vagus nerve.

19. The method of claim 14, wherein the stimulation comprises extremely low frequency, low level stimulation.

20. The method of claim 14, further comprising implanting a stimulator configured to apply stimulation to the subject's vagus nerve.

21. A method of treating and/or preventing a granulocyte-mediated disease or disorder in a subject, the method comprising:
   detecting a baseline granulocyte activation level; and
   applying a first stimulation to the subject's inflammatory reflex to inhibit granulocyte activation in response to the detected granulocyte activation level.

22. The method of claim 21, wherein the step of applying stimulation to the subject's inflammatory reflex comprises stimulating the subject's vagus nerve.

23. The method of claim 21, further comprising:
   detecting a second granulocyte activation level after a predetermined time after applying the first stimulation to the subject's inflammatory reflex;
   comparing the second granulocyte activation level with the baseline granulocyte activation level to determine a level of inhibition; and
   applying a second stimulation to the subject's inflammatory reflex when the level of inhibition exceeds a predetermined threshold.

24. The method of claim 21, wherein the step of detecting a granulocyte activation level comprises detecting expression of CD11b expression on granulocytes.

25. The method of claim 21, wherein the stimulation comprises mechanical stimulation.

26. The method of claim 21, wherein the stimulation comprises electrical stimulation.

27. The method of claim 21, wherein the stimulation comprises electromagnetic stimulation.

* * * * *